US00PP27293P3

(12) United States Plant Patent
Zaiger et al.

(10) Patent No.: US PP27,293 P3
(45) Date of Patent: Oct. 25, 2016

(54) INTERSPECIFIC TREE NAMED 'EMERALD BLUSH'

(50) Latin Name: **Interspecific *Prunus* Species**
Varietal Denomination: Emerald Blush

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 140 days.

(21) Appl. No.: 14/544,569

(22) Filed: Jan. 23, 2015

(65) Prior Publication Data

US 2016/0219770 P1 Jul. 28, 2016

(51) Int. Cl.
*A01H 5/06* (2006.01)

(52) U.S. Cl.
USPC ..... Plt./180

(58) Field of Classification Search
USPC ..... Plt./180
See application file for complete search history.

*Primary Examiner* — Keith Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Tree being a regular and productive bearer of medium size fruit.
3. Fruit with very good flavor and eating quality.
4. Fruit with an attractive green/yellow skin color.
5. Fruit with good storage and shipping qualities.

1 Drawing Sheet

Botanical designation: Interspecific *Prunus* species.
Variety denomination: 'Emerald Blush'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Amigo I' Interspecific (U.S. Plant Pat. No. 20,165), our non-patented proprietary interspecific seedlings '53LG662', '46GK97', '150LB26', '71GC117', '150LB5' and '14GD84'.

STATEMENT REGARDING FEDERALLY SPONSORED RESEARCH AND DEVELOPMENT

Not applicable.

ORIGIN OF THE VARIETY

The new and distinct variety of interspecific tree consists of the combination of *Prunus salicina* and *Prunus persica*.

It was originated by us in our experimental orchard located near Modesto, Calif. as a first generation cross between our proprietary non-patented interspecific seedling selections '53LG662' and '46GK97'. The non-patented interspecific seed parent (53LG662) originated from a cross between our proprietary non-patented interspecific seedling selections with the field identification numbers '150LB26' and '71GC117'. The non-patented interspecific pollen parent (46GK97) originated from a cross between our proprietary non-patented interspecific seedling selections '150LB5' and '14GD84'. A large number of these first generation seedlings were planted and maintained on their own root system and under close and careful observation the present seedling exhibited desirable fruit and tree characteristics and was selected in 2001 for additional asexual propagation and commercialization.

ASEXUAL REPRODUCTION OF THE VARIETY

In 2001 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct interspecific variety which includes [Plum×Plum Peach]×[Plum×Plum Peach] is of large size, vigorous, upright growth and a regular and productive bearer of medium size fruit with very good flavor and eating quality. The fruit is further characterized by its firm, yellow flesh, attractive green/yellow skin color and having good storage and shipping qualities. In comparison to its non-patented interspecific seed parent '53LG662' the tree of the new variety sets more fruit and the fruit has green/yellow skin compared to red. In comparison to its non-patented interspecific pollen parent '46GK97' the fruit of the new variety is approximately 20 days earlier in maturity. In comparison to the commercial variety 'Amigo I' Interspecific (U.S. Plant Pat. No. 20,165) the fruit of the new variety has a green/yellow skin color compared to red.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 13 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies with soil type, fertility of soil and climatic conditions.

*Form*.—Upright, usually pruned to vase shape.

*Branching habit*.—Upright growth, crotch angle approximately 35°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 11 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 400 hours at or below 45° F.

Trunk:

*Size*.—Medium. Average circumference 47.8 cm at 22.9 cm above ground on a 13 year old tree.

*Stocky*.—Medium stocky.

*Texture*.—Medium shaggy, roughness increases with age.

*Color*.—Varies from 10YR 4/2 to 5Y 3/2.

Branches:

*Size*.—Medium. Average circumference 7.9 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 24 in a 25.8 square cm area. Average length 3.1 mm. Average width 1.2 mm. Color 7.5YR 5/10.

*Color*.—New growth 5GY 5/8. Mature growth varies from 2.5Y 3/4 to 2.5Y 2/2, varies with age of growth.

Leaves:

*Size*.—Medium. Average length 103.8 mm. Average width 49.6 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 15.8 mm. Average width 2.0 mm. Longitudinally grooved. Surface — glabrous. Color varies from 5GY 4/6 to 10R 2/4.

*Glands*.—Type — globose. Size — small to medium. Average length 1.2 mm. Average diameter 0.8 mm. Number varies from 2 to 7, average number 4. Located primarily on the base of leaf blade and the upper portion of the petiole. Color 5GY 6/6.

*Stipules*.—Average number 2. Average length 10.9 mm. Edges — pectinate. Color 5GY 6/8.

*Color*.—Upper surface varies from 5GY 3/2 to 7.5GY 2/4. Lower surface varies from 5GY 3/2 to 7.5GY 3/2. Midvein color 5GY 6/4.

Flower buds:

*Size*.—Small to medium. Average length 9.3 mm. Average diameter 5.3 mm.

*Hardiness*.—Hardy with respect to California winters.

*Density*.—Very dense.

*Form*.—Conical, becoming elongated just before opening.

*Pedicel*.—Size — medium to large. Average length 9.0 mm. Average width 0.8 mm. Color varies from 2.5GY 6/6 to 5Gy 7/6. Surface — glabrous.

*Color*.—N 9.5/(white).

*Number of buds per spur*.—Average 12, varies from 8 to 20.

Flowers:

*Blooming period*.—Date of First Bloom Feb. 10, 2014. Date of Petal Fall Feb. 20, 2014, varies slightly with climatic conditions.

*Size*.—Medium. Average height 10.8 mm. Average diameter 23.3 mm.

*Petals*.—Normally 5, alternately arranged to sepals. Size — medium. Average length 11.0 mm. Average width 7.1 mm. Form — elliptical. Margin — entire. Arrangement free. Petal apex — rounded. Petal base — truncated. Color N 9.5/(white). Both upper and lower surfaces glabrous.

*Sepals*.—Normally 5, alternately arranged to petals. Size — small to medium. Average length 4.1 mm.

Average width 2.4 mm. Shape — triangular. Margin — entire. Sepal apex — rounded to triangular. Both upper and lower surfaces glabrous. Color — upper surface varies from 2.5GY 7/6 to 5GY 7/8. Lower surface varies from 2.5GY 7/6 to 5GY 7/8.

*Stamens*.—Average number per flower 31. Average filament length 7.8 mm. On average the height of the stamens are above the height of the petals. Filament color N 9.5/(white). Anther color varies from 10R 5/10 to 10R 4/12.

*Pollen*.—Self sterile, pollinator required. Color varies from 5Y 8/10 to 5Y 7/10.

*Pistil*.—Number — normally one. Surface — glabrous. Average length 8.1 mm. Position of stigma an average of 1.1 mm below anthers. Color varies from 10Y 8/6 to 2.5GY 8/6.

*Fragrance*.—Moderate.

*Color*.—N 9.5/(white).

*Pedicel*.—Average length 9.0 mm. Average width 0.9 mm. Color varies from 2.5GY 7/6 to 2.5GY 7/8. Surface glabrous.

*Number of flowers per flower bud*.—Average 3, varies from 1 to 4.

Fruit:

*Maturity when described*.—Firm ripe and ready for consumption.

*Date of first picking*.—Jul. 16, 2014.

*Date of last picking*.—Jul. 26, 2014, varies slightly with climatic conditions.

*Size*.—Medium. Average diameter axially 50.3 mm. Average transversely in suture plane 57.1 mm. Average weight 102.2 grams, varies slightly with fertility of the soil, amount of thinning and climatic conditions.

*Form*.—Globose.

*Suture*.—Nearly smooth.

*Ventral surface*.—Nearly smooth.

*Apex*.—Rounded.

*Base*.—Flat.

*Stem cavity*.—Rounded to slightly elongated in suture plane. Average depth 4.3 mm. Average diameter 5.9 mm.

Stem:

*Size*.—Small to medium. Average length 14.4 mm. Average diameter 2.1 mm.

*Color*.—Varies from 10Y 7/6 to 2.5GY 6/6.

Flesh:

*Ripens*.—Evenly.

*Texture*.—Firm to slightly soft.

*Fibers*.—Few, small, tender.

*Firmness*.—Firm, comparable to other commercial interspecific varieties.

*Aroma*.—Slight.

*Amydgalin*.—Undetected.

*Eating quality*.—Very good.

*Flavor*.—Very good, good balance between acid and sugar.

*Juice*.—Heavy amount, enhances flavor.

*Acidity*.—Not available.

*Brix*.—Average Brix 18.3°, varies slightly with amount of fruit per tree and climatic conditions.

*Color*.—Varies from 7.5Y 7/4 to 7.5Y 8/4.

*Pit cavity*.—Average length 22.4 mm. Average width 18.4 mm. Average depth 5.4 mm. Color varies from 5Y 6/6 to 2.5Y 6/6.

Skin:

*Thickness*.—Medium.

*Surface*.—Smooth.

*Bloom*.—Moderate amount, complete coverage.

*Tendency to crack*.—None.

*Color*.—Ground color varies from 10Y 6/8 to 2.5GY 4/6. Partially overspread with 7.5R 3/8 to 10Y 7/8.

*Tenacity*.—Tenacious to flesh.

*Astringency*.—Undetected.

Stone:

*Type*.—Clingstone, medium adherence to flesh.

*Size*.—Small to medium. Average length 21.8 mm. Average width 17.4 mm. Average thickness 10.0 mm.

*Form*.—Ovoid.

*Base*.—Flat.

*Apex*.—Slightly pointed. Average length 1.0 mm.

*Surface*.—Slightly pitted throughout. One shallow groove on each side of suture extending from base toward apex.

*Sides*.—Unequal, one side extending further outward from suture plane.

*Ridges*.—Very narrow, small ridge near groove on each side of suture.

*Tendency to split*.—None.

*Color*.—7.5YR 5/6 when dry.

Kernel:

*Size*.—Small. Average length 13.3 mm. Average width 10.2 mm. Average depth 5.7 mm.

*Form*.—Ovoid.

*Viability*.—Viable, complete embryo development.

*Skin color*.—Varies from 10Y 9/4 to 7.5Y 9/4.

Use: Dessert.

*Market*.—Local and long distance.

Keeping quality: Good, held firm in cold storage 3 weeks at 38° to 42° F. without internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

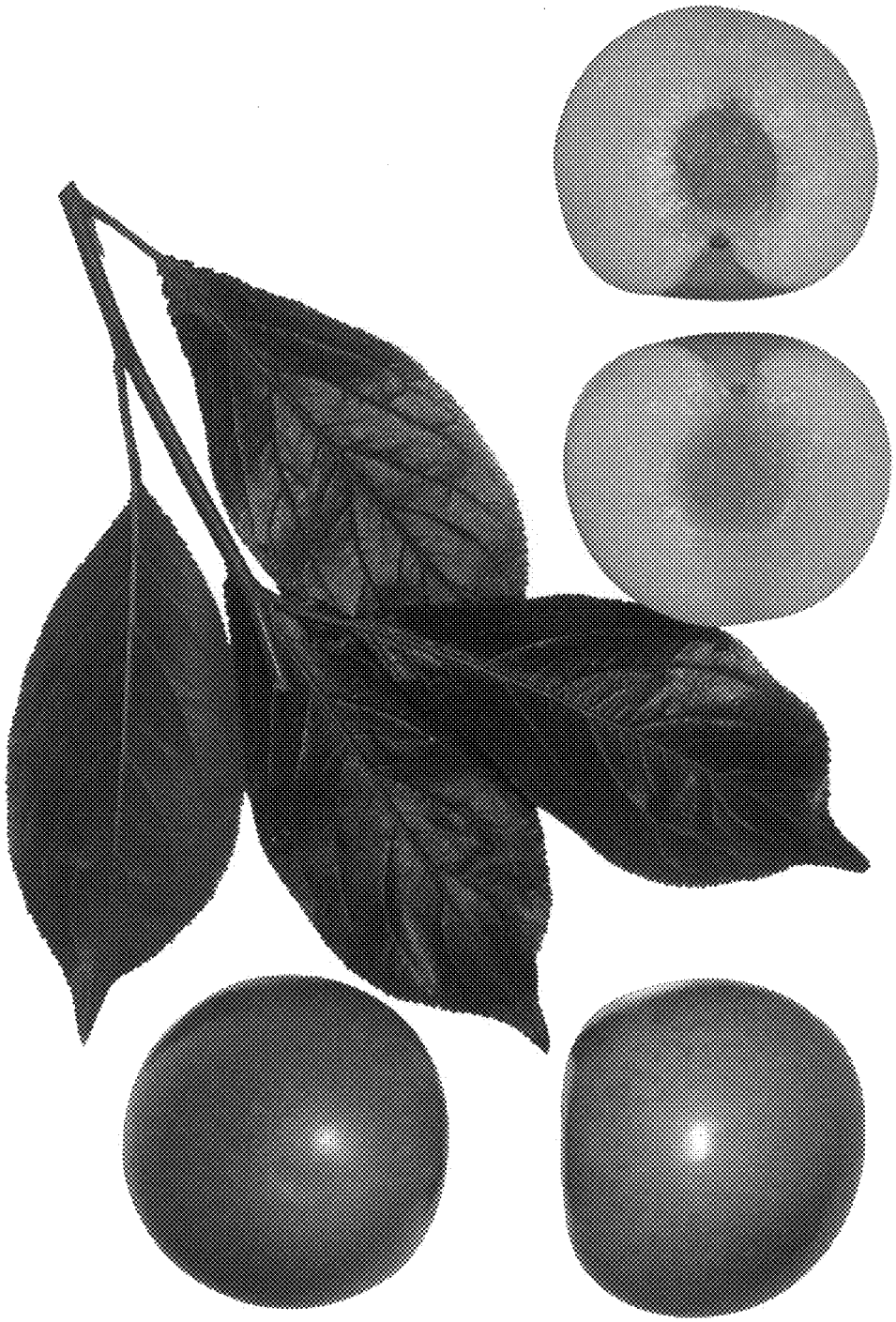

* * * * *